US009176067B2

(12) United States Patent
Milletari et al.

(10) Patent No.: US 9,176,067 B2
(45) Date of Patent: Nov. 3, 2015

(54) APPARATUS AND METHOD FOR DETERMINING THE EFFECTIVE CEMENTATION OR NITRIDING DEPTH OF STEEL COMPONENTS, IN PARTICULAR GEARS

(71) Applicant: GE AVIO S.r.l., Rivalta di Torino (IT)

(72) Inventors: Salvatore Milletari, Turin (IT); Salvatore Giunta, Turin (IT)

(73) Assignee: GE AVIO S.r.l., Turin (IT)

( * ) Notice: Subject to any disclaimer, the term of this patent is extended or adjusted under 35 U.S.C. 154(b) by 116 days.

(21) Appl. No.: 14/146,368

(22) Filed: Jan. 2, 2014

(65) Prior Publication Data

US 2014/0224991 A1 Aug. 14, 2014

Related U.S. Application Data

(63) Continuation of application No. PCT/IB2012/053422, filed on Jul. 4, 2012.

(30) Foreign Application Priority Data

Jul. 4, 2011 (IT) .............................. TO2011A0589

(51) Int. Cl.
*G01J 5/52* (2006.01)
*G01J 5/54* (2006.01)
*G01N 21/84* (2006.01)
*G01J 9/00* (2006.01)
(Continued)

(52) U.S. Cl.
CPC .............. *G01N 21/84* (2013.01); *G01B 21/085* (2013.01); *G01J 5/52* (2013.01); *G01J 9/00* (2013.01); *C21D 9/32* (2013.01); *G01J 2005/0048* (2013.01); *G01N 25/72* (2013.01)

(58) Field of Classification Search
CPC ........... G01N 21/84; G01N 25/72; G01J 5/52; G01B 21/085
See application file for complete search history.

(56) References Cited

U.S. PATENT DOCUMENTS 5,490,416 A * 2/1996 Adler ................................ 73/82
7,758,239 B2 * 7/2010 Ignatowicz ................... 374/139

(Continued)

OTHER PUBLICATIONS

Liu et al., "Transverse depth-profilometric hardness photothermal phase imaging of heat treated steels," Journal of Applied Physics, published Nov. 2003; Retrieved from internet [Jun. 24, 2015]; Retrieved from url <http://www.researchgate.net/publication/228996458>.*
Alan Hall: "An expanding market for CMM gear inspection," Jul. 1, 2009 p. 34, retrieved from the internet URL: www.geartechnology.com.

(Continued)

*Primary Examiner* — Yara B Green
(74) *Attorney, Agent, or Firm* — Davidson Berquist Jackson & Gowdey LLP

(57) ABSTRACT

An apparatus for determining the effective case-hardening or nitriding depth of a steel component comprises a measuring head, including a laser source generating a variable frequency radiation for the scanning of pre-determined portions of the component to be measured; an infrared detector, configured so as to detect infrared radiation generated by the component to be measured; and computing means of spectra of the infrared radiation received; and an evolventimeter, connected to the measuring head and including first computing means suitable for computing a hardness profile of the component to be measured on the basis of a launch profile and spectra of the infrared radiation received and second computing means suitable for computing the effective case-hardening depth from the hardness profile computed.

12 Claims, 5 Drawing Sheets

(51) Int. Cl.
  *G01B 21/08* (2006.01)
  *C21D 9/32* (2006.01)
  *G01J 5/00* (2006.01)
  *G01N 25/72* (2006.01)

(56) References Cited

U.S. PATENT DOCUMENTS

2002/0011852 A1* 1/2002 Mandelis et al. ............. 324/752
2009/0154521 A1* 6/2009 Wang et al. .................... 374/53
2012/0043962 A1* 2/2012 Wang et al. ................... 324/239

OTHER PUBLICATIONS

Hong Qu et al: Reconstruction of depth profiles of thermal conductivity of case hardened steels using a three-dimensional photothermal technique, Journal of Applied Physics, vol. 104, No. 11, Jan. 1, 2008 p. 113518, XP055018549.
PCT/IB2012/053422, International Search Report and Written Opinion, mailed Mar. 6, 2013.
PCT/IB2012/053422, Written Opinion of the International Preliminary Examining Authority.

* cited by examiner

APPARATUS AND METHOD FOR DETERMINING THE EFFECTIVE CEMENTATION OR NITRIDING DEPTH OF STEEL COMPONENTS, IN PARTICULAR GEARS

CROSS-REFERENCE TO CO-PENDING APPLICATION

This application is a continuation of co-pending PCT Application PCT/IB2012/053422, filed Jul. 4, 2012 designating the United States, which claims priority to Italian Patent Application No. TO2011A000589, filed Jul. 4, 2011. The contents of both of those applications are incorporated herein by reference.

TECHNICAL FIELD

The present invention relates to an apparatus and method for determining the effective case-hardening or nitriding depth of steel components, in particular gears.

BACKGROUND ART

As is known, some applications require high hardness steel gears. For this purpose, the steel undergoes a hardening process consisting of a phase of case-hardening or nitriding of the surface and subsequent thermal treatment of the steel component. This process achieves a partial structural transformation of the steel from austenite to martensite, the grains of which make the steel harder. From a thermal point of view, the presence of grains of martensite inhibits the transport of heat due to the high thermal contact resistance at the edge of the grain.

The macroscopic result is that as the martensite content increases, the hardness of the steel increases and the conductivity and thermal diffusivity decrease. The case-hardening and/or nitriding depth is a gear design requirement and it must therefore be measured at the testing stage.

Currently, to evaluate the hardness of the samples at the end of the hardening process, the effective case-hardening or nitriding depth is measured both after the thermal treatment and downstream of the further steel machining phases, typically downstream of the final gear grinding operation.

For this purpose, after the thermal treatment, the hardness profile is determined using a durometer on the central section of a cylindrical test piece which accompanies the batch during case-hardening or nitriding; after the final grinding, the hardness profiles are determined on the tooth sides, on the root radius, on the top land and on the end face, of three teeth arranged at 120° and on the gear bearing track.

In both cases, before determination of the hardness profiles by means of the durometer, preliminary operations are necessary which entail sectioning of the gear and cylindrical test piece, enclosure in resin and polishing.

The current method for determining the hardness is disadvantageous, since it is of the destructive type and entails sectioning of the gear. Furthermore, it is costly and lengthy, due to the presence of a series of preliminary operations for preparation of the samples to be measured.

The article "Reconstruction of depth profiles of thermal conductivity of case hardened steels using a three-dimensional photothermal technique", by Hong Qu and others, Journal of Applied Physics, vol. 104, no. 11, Jan. 1, 2008, p. 113518 describes a method for determining the effective case-hardening depth. In particular, the method described entails a non case-hardened sample and a plurality of case-hardened samples having known and different effective case-hardening depths. Furthermore, a laser source transmits electromagnetic radiation excitation, at variable frequency, to each case-hardened sample; therefore, each case-hardened sample generates an electromagnetic radiation in response. According to the method, a spectrum is furthermore determined for each case-hardened sample; this spectrum is equal to the difference between the phase of the electromagnetic response radiation generated by the case-hardened sample considered and the phase generated by the electromagnetic response radiation generated by the non case-hardened sample, this difference being a function of the frequency of the electromagnetic excitation radiation. For each spectrum a corresponding minimum and the corresponding frequency at which this minimum occurs are therefore computed; in this way, the number of minimum frequencies will correspond to the number of case-hardened samples. A calibration function is then determined, which correlates the minimum frequencies with the effective case-hardening depths of the corresponding case-hardened samples. The electromagnetic radiation excitation is then transmitted to the unknown sample, so that the unknown sample generates a respective electromagnetic response radiation. A further spectrum is subsequently determined, equal to the difference between the electromagnetic response radiation phase generated by the unknown sample and the electromagnetic response radiation phase generated by the non case-hardened sample, this difference being a function of the frequency of the electromagnetic radiation excitation. Lastly the minimum of this further spectrum is determined, and the corresponding frequency at which this minimum occurs. By comparison between the minimum frequency of the unknown sample and the above-mentioned calibration function, the effective case-hardening depth of the unknown sample is estimated.

Although the method described is of the non-destructive type, it provides results that depend largely on the precision with which the minimum frequencies of the known case-hardened samples are determined. Unfortunately, however, determination of the minimum frequencies may be imprecise and therefore the calibration function may not be accurate. Furthermore, the calibration function has a high slope; consequently, the inevitable inaccuracies in determination of the minimum frequency of the unknown sample entail considerable variations in the effective case-hardening depth determined.

DISCLOSURE OF INVENTION

The object of the present invention is to make available an apparatus and a method for measuring the effective case-hardening or nitriding depth which solves the drawbacks of the known methods.

According to the present invention, an apparatus is produced for determining the effective case-hardening or nitriding depth of a steel component, as defined in claim 1. Furthermore, according to the present invention, a method is provided for determining the effective case-hardening or nitriding depth of a steel component, as defined in claim 8.

BRIEF DESCRIPTION OF THE DRAWINGS

The invention will now be described with reference to the accompanying drawings, which illustrate non-limiting embodiment examples, in which.

BEST MODE FOR CARRYING OUT THE INVENTION

The present invention is based on a measuring technique PTR (Laser Photothermal Radiometry), consisting in exciting the area of the component to be measured with a frequency-modulated laser source. The thermal waves generated penetrate into the hardened steel and are reflected by the material; consequently, the material generates infrared radiation.

In particular, the penetration depth of the laser radiation depends on its frequency. Furthermore, the infrared radiation emitted depends on the hardness of the area reflecting each time; therefore, by scanning the area of the gear to be measured with a differentiated frequency laser radiation, at each moment the infrared radiation is correlated with the specific hardness of the region struck at that moment by the laser radiation. An infrared detector, for example cadmium mercury telluride, and appropriate processing electronics collect this infrared radiation and determine the spectrum of this infrared radiation, and in particular determine the amplitude and phase of the infrared radiation emitted; in further detail, the processing electronics determine the difference between the phase of infrared radiation emitted by the component and the phase of the infrared radiation emitted by a non case-hardened (known) component, in addition to the difference between the amplitude of the infrared radiation emitted by the component and the amplitude of the infrared radiation emitted by the non case-hardened component, as described in further detail below. Separately, initial case-hardening or nitriding parameters are acquired, as explained below; on the basis of the initial parameters, an initial hardness profile is generated, called launch profile, which is corrected in several steps taking account of the spectra detected and the relation (known) between the diffusivity of the gear material and the local hardness; this relation is determined in a per se known manner experimentally, for example via photothermal deflection on samples with profiles of known hardness. By means of an iterative process, a reconstructed hardness profile is obtained having a thermal spectrum similar to the one measured. The depth at which said reconstructed hardness profile has a value equal to 513 HV constitutes, by definition, the effective case-hardening or nitriding depth E, in turn defined as core hardness+100 HV.

Figure 1:
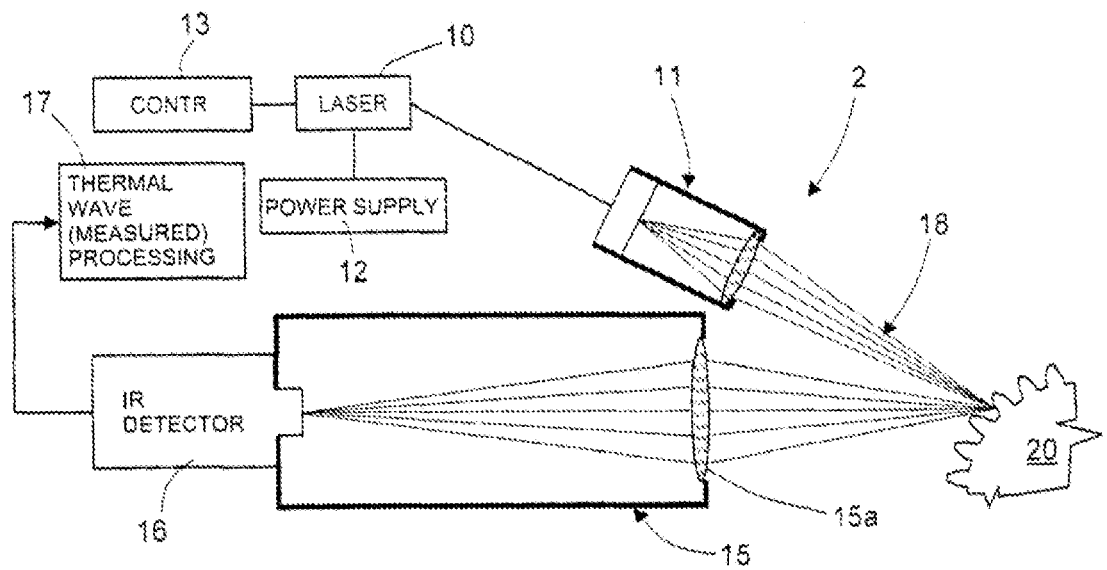
FIG. 1 shows a schematic diagram of a measuring head belonging to the present apparatus.
Figure 2:
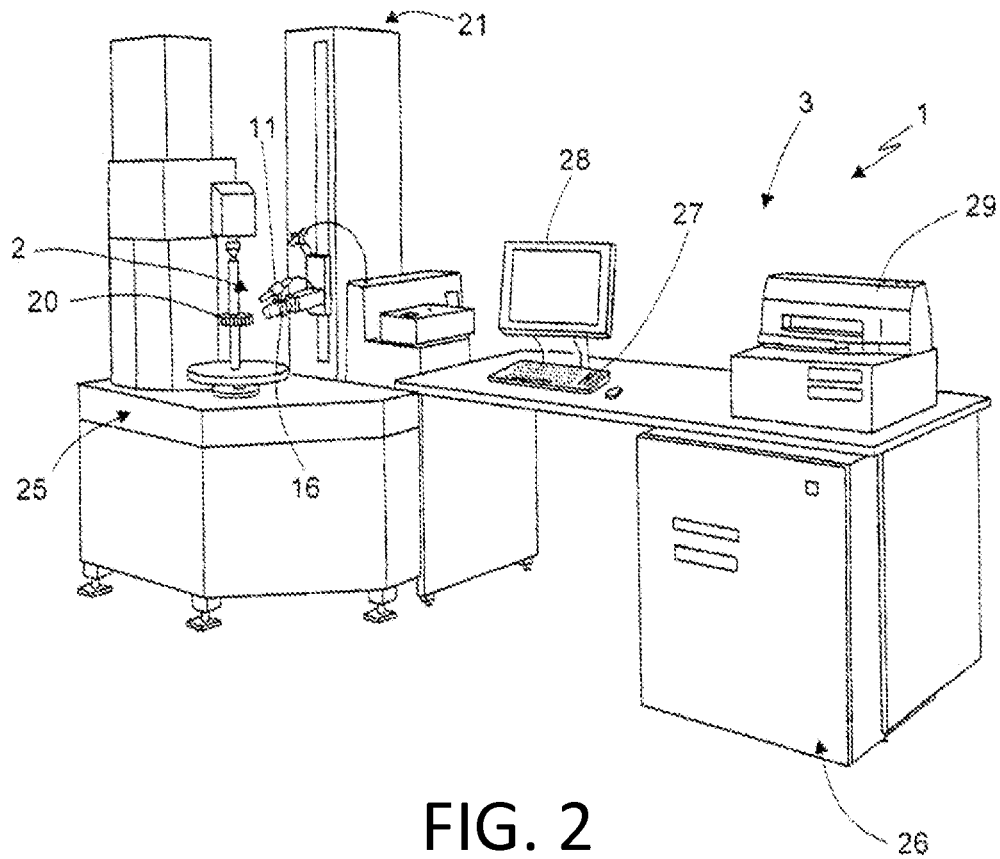
FIG. 2 shows an implementation of an evolventimeter belonging to the present apparatus.

In order to implement the above technique, the present apparatus 1 (FIG. 2) comprises two parts: a measuring head 2, schematised in FIG. 1, and an evolventimeter 3, shown in FIG. 2.

In detail, the measuring head 2 comprises a laser source 10, connected to a laser collimator 11, to a power supply 12 and to a controller 13. The laser source 10 is also connected to a thermoelectric type cooling control system, not shown. Furthermore, the measuring head 1 comprises a focuser 15, an IR detector 16 and a spectrum computing unit 17, which is also referred to as the processing unit 17.

For example, in a prototype produced by the applicant, the measuring head 2 has been optimised so that the distance D1 between the focus F and the lens L1 of the laser collimator is 27 mm, the distance between the lens L1 and the gear 20 is 77 mm and the distance between the gear 20 and the IR detector 16 is equal to 200 mm. The IR detector 16 is of HgCdTe type.

Figure 3:
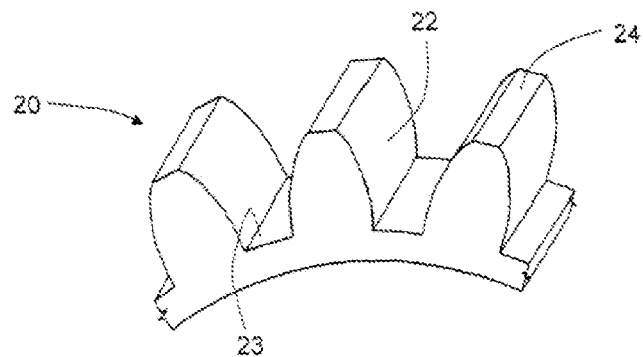
FIG. 3 shows a portion of a gear and the areas on which the measurements are taken.

The measuring head 2 is moved by means of the evolventimeter 3 (as shown only schematically by a movement unit 21, in a manner that can be easily understood by a person skilled in the art) so as to allow the laser beam 18 emitted by the laser collimator 11 to scan a gear 20, namely the tooth sides 22, the root radius 23 and the top land 24 (FIG. 3) of each individual tooth at different frequencies.

As indicated above, this frequency scanning (for example from 1000 Hz to 0 Hz and with logarithmic trend) determines the emission, by the material of the gear 20 positioned at a different distance from the surface, of a corresponding infrared radiation (also known as thermal wave) which, focused via a lens 15a of the focuser 1, is detected by the detector IR 16, which generates corresponding electric signals. These signals are then processed by the processing unit 17 to obtain the trend of the phase and of the thermal wave amplitude, indicated below as spectra measured and shown for example in FIGS. 4A and 4B respectively.

In further detail, the processing unit 17 determines a first and a second measured spectrum of the infrared radiation received, which is emitted by a portion of the gear 20 identified, in a per se known manner, by the evolventimeter 3. The distance between the identified portion of the gear 20 and the laser source 10 is maintained constant during the frequency scanning operations.

Before describing the first and the second spectrum measured, it should be noted that determination of the first and second spectrum measured is preceded by determination of the trends (as the frequency of the laser source 19 varies) of the phase and amplitude of the infrared radiation emitted by a non case-hardened gear (not shown), and in particular by a portion of this non case-hardened gear identified by the evolventimeter 3 and corresponding to the above-mentioned portion of the gear 20. The non case-hardened gear is formed of the same material as the gear 20, but it is not case-hardened; furthermore the non case-hardened gear has the same geometrical shape as the gear 20.

During the frequency scanning, the distance between the laser source 10 and the identified portion of the non case-hardened gear does not vary. Below, for the sake of brevity, we refer to the emission of infrared radiation by the gear 20 and the non case-hardened gear, with the reference to the corresponding portions identified by the evolventimeter 3 being understood.

The first spectrum measured is equal to the difference between the phase of the infrared radiation generated by the gear 20 and the phase of the infrared radiation generated by the non case-hardened gear, this difference being a function of the frequency of the radiation generated by the laser source 10. The second spectrum measured is equal to the difference between the amplitude of the infrared radiation generated by the gear 20 and the amplitude of the infrared radiation generated by the non case-hardened gear, this difference being a function of the frequency of the radiation generated by the laser source 10.

Figure 5:
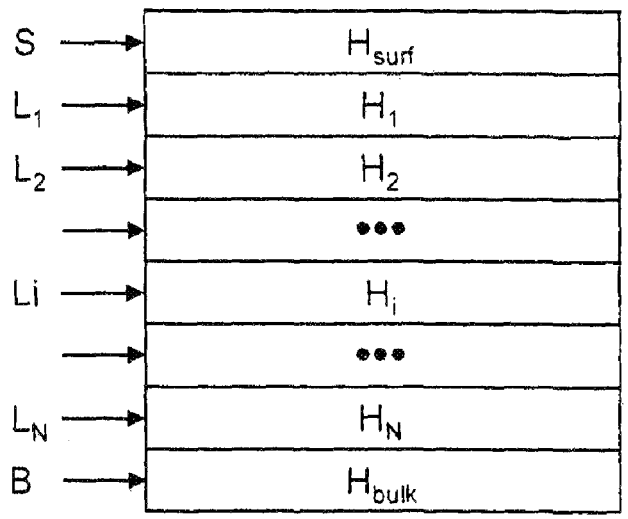
FIG. 5 shows modelling of the physical structure of the gear portion to be analysed using the present method.

In further detail as shown in FIG. 5, the part of the gear to be analysed is schematised as formed of a sequence of N+2 layers including a surface layer S, having hardness $H_{surf}$, a core layer B, having hardness $H_{bulk}$, and N intermediate layers $L_i$, each of which is modelled by a uniform structure inside the respective layer and having a respective hardness Hi, with i=1, 2, ..., N, constant inside each layer. The N intermediate layers $L_i$ have equal thickness, e.g. 0.1 mm; in each of them, therefore, the thermal diffusivity is considered constant.

Figures 7A, 7B:
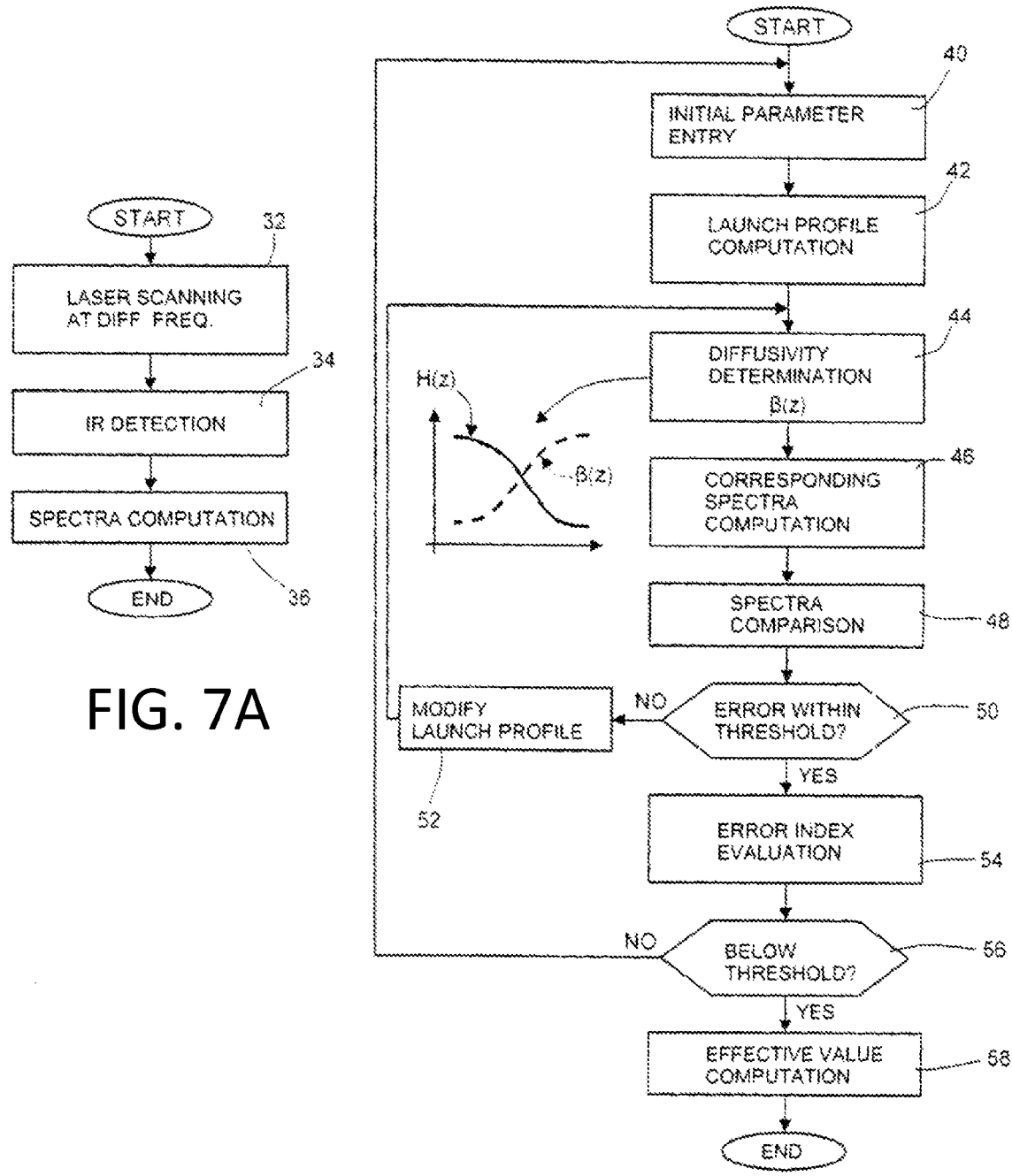
FIGS. 7A and 7B show flow charts of the present method of determination of the effective depth.

In this hypothesis, the measuring head 2 performs the steps shown in the flow chart of FIG. 7A and comprising the phases of: scanning, with a variable frequency laser radiation, predetermined portions of the component to be measured, step 32; detecting the infrared radiation generated by the component to be measured in response to the laser scanning, step 34; and determining the spectra of the infrared radiation received (i.e. the above-mentioned first and second spectrum measured), step 36.

The evolventimeter 3 (FIG. 2) comprises, in addition to a support bench 25 for the measuring head 2, a calculator 26 (which provides for movement of the measuring head 2 and can also incorporate the spectra calculation unit 17 of FIG. 1) and input/output interface units for interaction with an operator, such as a keyboard 27, a screen 28, a printer 29, etc.

Figure 6:
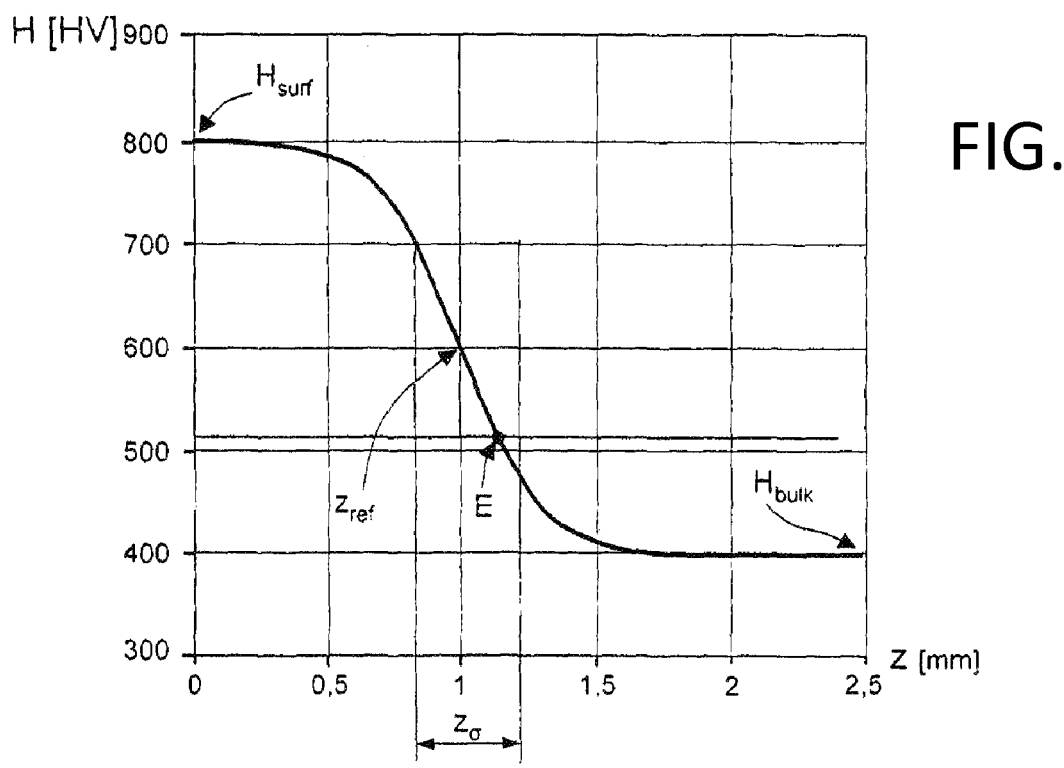
FIG. 6 shows an initial hardness profile used by the present method.

The processing unit 17 furthermore implements an algorithm to determine the hardness profile reconstructed starting from the hypothesis of homogeneity of the intermediate layers $L_i$, as discussed above and using initially a launch profile $H_L$ (according to the variable z, distance from the surface) set so as to be representative of the profiles expected for all the steels examined, belonging to the class of decreasing monotonic profiles provided by the expression:

$$H_L(z) = \frac{H_{surf} + H_{bulk}}{2} - \left(\frac{H_{surf} - H_{bulk}}{2}\right) \tanh\left(\frac{z - z_{ref}}{z_\sigma}\right) \quad (1)$$

the trend of which is shown in FIG. 6, which also shows the meaning of the parameters used.

In particular, in the equation (1), $H_{surf}$ and $H_{bulk}$ are the hardness values of the surface layer S and of the core layer B, as indicated above, and are set by the user, according to experience, as expected surface hardness, asymptotic hardness, effective case-hardening depth and thermal treatment performed on the gear, for example by using default values associated with the type of steel in question; $z_{ref}$ represents the depth of the martensite/austenite interface, i.e. the depth at which the launch profile reaches the hardness halfway between $H_{surf}$ and $H_{bulk}$; and $z_o$ is the thickness of the transition region between martensite and austenite, therefore the slope of the profile in that region. For practical purposes, $H_{surf}$ and $H_{bulk}$ are set according to corresponding expected values, which depend on the thermal case-hardening treatment which the gear 20 has undergone.

Starting from this launch profile $H_L$, the processing unit 17 calculates the hardness profile reconstructed by means of an inversion process described below with reference to the flow chart of FIG. 7B.

In detail, the processing unit 17 runs a program, which initially waits for entry of the values of the parameters $H_{surf}$, $H_{bulk}$, $z_o$, $z_{ref}$, step 40, and generates the corresponding launch profile H(z), step 42. On the basis of the known relation between each value of the hardness H and the thermal diffusivity $\beta$, obtained previously on the basis of measurements performed on test pieces with known hardness and stored in tables not shown, the program computes the trend of the thermal diffusivity for each layer $L_1$-$L_N$ of the gear in question, step 44, and determines thermal launch spectra of the thermal wave, step 46.

In particular, a first and a second thermal launch spectrum are determined, associated with the launch profile and determined on the basis of the thermal equation described below.

The first thermal launch spectrum is equal to the difference between the infrared radiation phase generated by a theoretical gear, which has a hardness profile equal to the launch profile, and the infrared radiation phase generated by the non case-hardened gear; the first thermal launch spectrum reports said difference as the frequency of the laser source varies. In particular, the infrared radiation phase generated by the theoretical gear is calculated numerically, as described below, in the hypothesis that this infrared radiation is generated by a portion of the theoretical gear which corresponds to the above-mentioned portion of the gear 20.

The second thermal launch spectrum is equal to the difference between the amplitude of the infrared radiation generated by the theoretical gear and the amplitude of the infrared radiation generated by the non case-hardened gear; also the second thermal launch spectrum is a function of the frequency of the laser source 10. Furthermore, the amplitude of the infrared radiation generated by the theoretical gear is computed numerically, in the same hypotheses as previously.

In detail, the theoretical gear is a physical-mathematical model of a real gear, which has a hardness profile equal to the launch profile. Furthermore, while the phase and amplitude of the infrared radiation generated by the non case-hardened gear are determined on the basis of measurements of this radiation, the phase and amplitude of the infrared radiation generated by the theoretical gear are obtained numerically, i.e. in the absence of a real gear equal to the theoretical gear.

Again in further detail, for calculation of the thermal launch spectra, and in particular for calculation of the phase and amplitude of the infrared radiation generated by the theoretical gear, the program uses the thermal wave equation:

$$\nabla^2 \Phi(z,\omega) - \sigma^2(\omega)\Phi(z,\omega) = Q(z,\omega) \quad (2)$$

in which $\Phi$ is the infrared radiation of which the amplitude A and the phase $\phi$ will be obtained according to the scanning frequency f and layer depth considered z; $\sigma$ is a complex wave diffusion number connected with the thermal diffusivity $\beta(z)$ by the relation:

$$\sigma(\omega) = \frac{1+i}{(2\beta(z)/\omega)^{\frac{1}{2}}} \quad (3)$$

with $\omega = 2\pi f$; and Q is the power or the temperature of the laser source used, known.

Figure 4A:
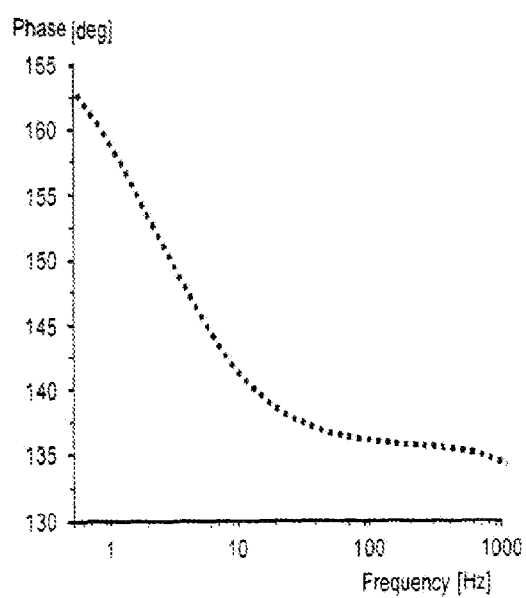
FIGS. 4A and 4B show examples of spectra measured by the measuring head of FIG. 1.
Figure 4B:
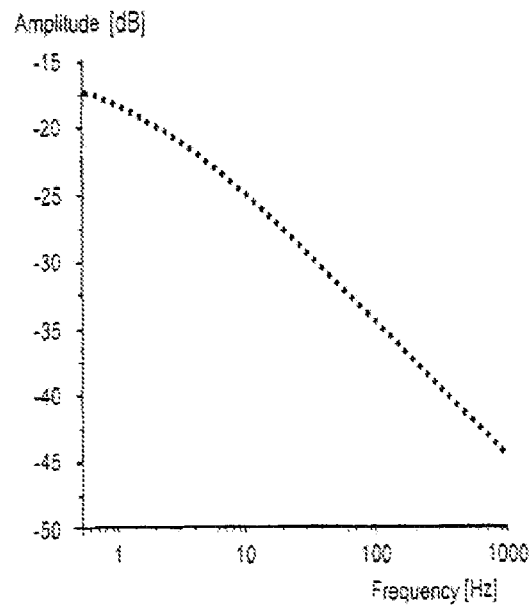

In particular, (2) is solved by using known mathematical inversion methods, generating spectra similar to those shown in FIGS. 4A and 4B.

The thermal launch spectra just computed are then compared with the previously obtained spectra measured, step 48; if the difference between the spectra is below a threshold, output NO from step 50, the trend of the launch profile is modified, step 52. By way of example, an overall value can be computed equal to the sum (weighted, if necessary) of a first and a second value, the first value being proportional to the integral of the difference between the first spectrum measured and the first thermal launch spectrum, the second value being proportional to the integral of the difference between the second spectrum measured and the second thermal launch spectrum.

The program then returns to step 44 to determine the diffusivity associated with the new launch profile and repeats steps 46-50 until a hardness profile is identified correlated with thermal launch spectra similar to those measured (output YES from step 50) or after a certain number of iterations.

At the end of the inversion algorithm, an overall error index is evaluated, step 54. For example, the error index takes into account any presence of oscillations in the trend of the hardness profile computed H(Z) (not conforming to the real physical behaviour), the error existing between the hardness profile computed and a hardness profile stored, statistically determined by measurements previously performed with other means (for example durometer) and similar.

If the error index is excessive (output NO from step 56), the program goes back to step 40 and awaits different parameters. In this phase the operator, on the basis of experience and/or progressive default modifications, modifies the initially set parameters, discussed previously, activating a new inversion phase.

Vice versa, if the error index is acceptable (output YES from step 56), the program provides, as effective case-hardening value, the distance Z at which the value of the hardness profile H(z) computed is equal to 513 HV, step 58.

Figure 8:
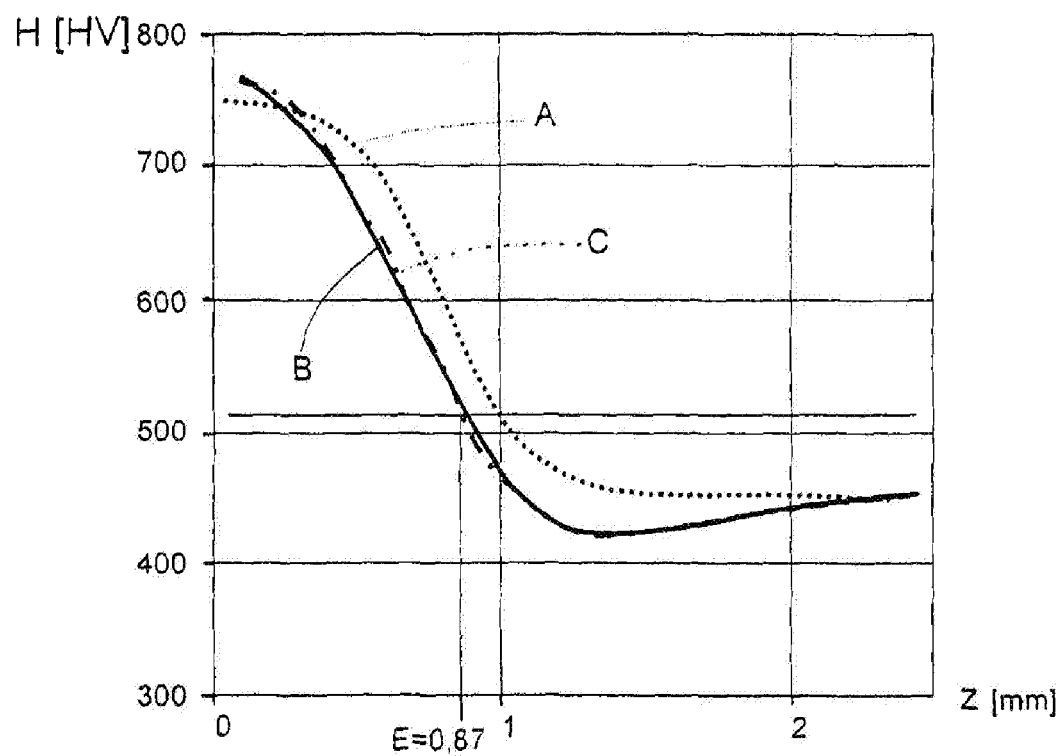
FIG. 8 shows the comparison between the hardness profile determined by the present method and reference profiles measured by means of durometer.

For example, FIG. 8 shows a comparison between a launch profile A, obtained by setting the initial parameters in the equation (1), a hardness profile computed B, obtained with the algorithm of FIG. 7, and a hardness profile C measured with a durometer, according to the known technique. As can be noted, starting from the curve A, with the present apparatus and method a reconstruction is achieved which is very similar to the one that can be obtained by means of durometer, but with a considerable saving in time and costs.

On the one hand the apparatus and method described here are non-destructive, and they can therefore operate directly on the pieces produced, without the costs of purposely-provided samples which are destroyed and therefore cannot be placed on the market; on the other, the measuring operation (if we assume the measurement of two teeth of a gear 20 in the three positions indicated above) requires a much shorter time than the known solution (approximately 2 hours instead of over 18 hours).

It should be furthermore noted that use of the evolventimeter allows the non case-hardened gear and the gear 20 to be successively positioned at the same distance from the measuring head. Furthermore, independently of the region of the gear 20 to be measured, it is possible to accurately position this region at a pre-defined distance from the measuring head.

This means that the average lead time (i.e. the total time elapsing between two or more piece machining phases) is reduced from eight days with the known method to one day with the present method and apparatus, given that it now depends only on the time required to perform the hardness measurement described above.

Lastly it is clear that modifications and variations can be made to the apparatus and method described and illustrated here without departing from the protective scope of the present invention, as defined in the attached claims.

The invention claimed is:

1. Apparatus for determining the effective case-hardening or nitriding depth of a steel gear to be measured, comprising:
    an evolventimeter suitable for identifying a portion of said gear to be measured and of a reference gear of the non case-hardened non-nitrided type; and
    a measuring head connected to the evolventimeter and including a laser source configured to generate a variable frequency radiation for scanning portions of the gear to be measured and of the reference gear identified by the evolventimeter;
and wherein said measuring head furthermore comprises:
    an infrared detector configured to detect infrared radiation generated by the gear to be measured and by the reference gear in response to scanning by the laser source;
    first processing means configured to determine, on the basis of the infrared radiation detected, at least one between a first and a second measured spectrum, the first measured spectrum indicating the difference between the phase of the infrared radiation generated by the gear to be measured and the phase of the infrared radiation generated by the reference gear, the second measured spectrum indicating the difference between the amplitude of the infrared radiation generated by the gear to be measured and the amplitude of the infrared radiation generated by the reference gear;
    first computing means configured to compute a calculated hardness profile of the gear to be measured, on the basis of a launch profile equal to a first hardness profile, and of said at least one between the first and the second measured spectrum; and
    second computing means configured to compute the effective case-hardening or nitriding depth, on the basis of the calculated hardness profile.

2. An apparatus according to claim 1, wherein the first computing means comprise:
    means for determining a diffusivity profile corresponding to the launch profile;
    third computing means configured to perform an inversion algorithm to calculate, on the basis of a thermal equation, the phase and amplitude of infrared radiation generated by a theoretical gear having hardness profile equal to the launch profile;
    second processing means configured to determine at least one between a first and a second thermal launch spectrum associated with the launch profile, the first thermal launch spectrum indicating the difference between the computed phase of the infrared radiation generated by the theoretical gear and the phase of the infrared radiation generated by the reference gear, the second thermal launch spectrum indicating the difference between the computed amplitude of the infrared radiation generated by the theoretical gear and the amplitude of the infrared radiation generated by the reference gear;
    comparison means configured to compare said at least one between the first and second thermal launch spectrum with said at least one between the first and second measured spectrum; and
    correction means of the launch profile on the basis of the comparison made by the comparison means.

3. The apparatus according to claim 2, wherein the first processing means are configured to determine both the first and the second measured spectrum, and the second processing means are configured to determine both the first and the second thermal launch spectrum; and wherein the comparison means are configured to compare the first and the second thermal launch spectrum with the first and the second measured spectrum respectively.

4. The apparatus according to claim 1, wherein the evolventimeter comprises means for movement of the measuring head.

5. The apparatus according to claim 1, wherein the launch profile is a hyperbolic tangent type decreasing monotonic function of the distance from the surface of the gear to be measured.

6. The apparatus according to claim 1, wherein the first computing means are configured to perform an iterative process.

7. The apparatus according to claim 1, wherein the measuring head is mounted on the evolventimeter.

8. A method for determining the effective case-hardening or nitriding depth of a steel gear, comprising the steps of:
identifying a portion of said gear to be measured and of a reference gear of non case-hardened non-nitrided type;
scanning with a variable frequency laser radiation the identified portions of the gear to be measured and of the reference gear;
detecting infrared radiation generated by the gear to be measured and by the reference gear in response to the laser scanning;
determining, on the basis of the infrared radiation detected, at least one between a first and a second measured spectrum, the first measured spectrum indicating the difference between the phase of the infrared radiation generated by the gear to be measured and the phase of the infrared radiation generated by the reference gear, the second measured spectrum indicating the difference between the amplitude of the infrared radiation generated by the gear to be measured and the amplitude of the infrared radiation generated by the reference gear;
acquiring a first hardness profile;
generating a launch profile on the basis of said first hardness profile;
determining a computed hardness profile of the gear to be measured, modifying the launch profile on the basis of said at least one between the first and the second measured spectrum; and
determining the effective case-hardening or nitriding depth, on the basis of the hardness profile computed.

9. The method according to claim 8, wherein the step of determining a computed hardness profile comprises the steps of:
determining a diffusivity profile associated with the launch profile;
performing an inversion algorithm to compute, on the basis of a thermal equation, the phase and amplitude of infrared radiation generated by a theoretical gear having hardness profile equal to the launch profile;
determining at least one between a first and a second thermal launch spectrum associated with the launch profile, the first thermal launch spectrum indicating the difference between the computed phase of the infrared radiation generated by the theoretical gear and the phase of the infrared radiation generated by the reference gear, the second thermal launch spectrum indicating the difference between the computed amplitude of the infrared radiation generated by the theoretical gear and the amplitude of the infrared radiation generated by the reference gear;
comparing said at least one between the first and the second thermal launch spectrum with said at least one between the first and the second measured spectrum; and
correcting the launch profile on the basis of the comparison made.

10. The method according to claim 9, furthermore comprising determining both the first and the second measured spectrum, and determining both the first and the second thermal launch spectrum; and wherein said comparison step comprises comparing the first and the second thermal launch spectrum with the first and the second measured spectrum respectively.

11. The method according to claim 9, wherein the step of determining a diffusivity profile comprises associating with each point of the launch profile a diffusivity value on the basis of tests performed on test pieces with known hardness.

12. The method according to claim 8, wherein the launch profile is a hyperbolic tangent type decreasing monotonic function of the distance from the surface of the gear to be measured.

* * * * *